United States Patent [19]
Lennox et al.

[11] Patent Number: 4,955,377
[45] Date of Patent: Sep. 11, 1990

[54] DEVICE AND METHOD FOR HEATING TISSUE IN A PATIENT'S BODY

[76] Inventors: Charles D. Lennox, 75 Ledgewood Hills Dr., Nashua, N.H. 03062; Richard A. Noddin, 1390 Washington St., Holliston, Mass. 01746; Ronald Sahatjian, 29 Saddle Club Rd., Lexington, Mass. 02173

[21] Appl. No.: 263,815

[22] Filed: Oct. 28, 1988

[51] Int. Cl.$^5$ .............................................. A61F 7/12
[52] U.S. Cl. ................................... 128/401; 606/27
[58] Field of Search ........ 128/303.1, 303.12, 399–402, 128/784–786, 804; 606/27–31

[56] References Cited

U.S. PATENT DOCUMENTS

| | | | |
|---|---|---|---|
| 3,011,872 | 3/1977 | Komiya | 128/303.14 |
| 3,920,021 | 11/1975 | Hiltebrandt | 128/303.17 |
| 4,142,529 | 3/1979 | Latenser et al. | 128/303.12 |
| 4,160,455 | 7/1979 | Law | 128/400 |
| 4,227,535 | 10/1980 | Connor | 128/303.13 |
| 4,397,314 | 8/1983 | Vaguine | 128/399 |
| 4,532,924 | 9/1985 | Auth et al. | 128/303.17 |
| 4,676,258 | 6/1987 | Inokuchi et al. | 128/401 |

FOREIGN PATENT DOCUMENTS

8100176  3/1981  PCT Int'l Appl. .

OTHER PUBLICATIONS

R. L. Protell et al., Computer-Assisted Electrocoagulation: Bipolar vs Monopolar in the Treatment of Experimental Gastric Ulcer Bleeding, Nov. 1978.

Moore et al., Evaluation of Bipolar Electrocoagulation in Canine Stomachs, vol. 24, No. 4, 1978, pp. 148–151.

*Primary Examiner*—Max Hindenburg
*Attorney, Agent, or Firm*—Fish & Richardson

[57] ABSTRACT

Device and method for heating tissue, the device having a catheter shaft for insertion into a patient's body, a chamber formed by a collapsible balloon mounted on the catheter shaft and filled with an electrically conductive fluid, two or more electrical contacts enclosed within the chamber, a power supply for applying an electrical potential to the contacts, and a two or more conductors for connecting each of the contacts to the power supply. The fluid is heated on the basis of $I^2R$ losses by a radio frequency electric current flowing between the electrodes, and the fluid in turn heats the surrounding tissue by heat transfer through the wall of the chamber. According to the method, the apparatus is inserted into the patient's body, the chamber is filled with an electrically conductive fluid, and an electrical potential is applied to the contacts. The apparatus functions as a temperature source. A thermister sensor in the balloon or in contact with tissue responds to the heating effect to control the application of the current. Advantageously, by periodic sensing of temperature, and application of controlled rf power, a preset constant temperature is maintained at the selected sensing point, either at the internal body site or the liquid within the balloon. In this way carefully controlled therapy can be conducted at constant temperature.

27 Claims, 5 Drawing Sheets

DEVICE AND METHOD FOR HEATING TISSUE IN A PATIENT'S BODY

BACKGROUND OF THE INVENTION

This invention relates to balloon catheters and similar devices useful to apply heat within a patient's body, e.g. for angioplasty, hyperthermal treatment of tumors, and other medical procedures.

Prior proposals for application of heat internally of the body often have had drawbacks. The devices have been too large for certain procedures or have otherwise been difficult to insert, remove or control. In some cases, the devices have been too complex in construction or have been too expensive.

We have conceived of an approach that, in a number of circumstances, can overcome such drawbacks.

SUMMARY OF THE INVENTION

In one aspect the invention features a device and method for heating tissue employing a chamber constructed for insertion into a patient's body, an electrically conductive fluid preselected to produce resistive heating for filling the chamber, a plurality of spaced electrical contacts enclosed within the chamber and a corresponding plurality of conductors for connecting the electrical contacts to a power supply for applying a radio frequency electrical potential to the contacts, the contacts being exposed to the fluid-containing space of the chamber so that radio frequency electrical potential can cause current to flow through fluid between the contacts, the chamber and the electrical contacts being cooperatively constructed and arranged to cause the current to be substantially confined to the fluid within the chamber, whereby on the basis of $I^2R$ losses of the radio frequency electric current flowing between the electrical contacts, the fluid can be heated, and the fluid in turn can heat the surrounding tissue by thermal conduction through a wall of the chamber.

Another aspect of the invention is a catheter device constructed to operate in the above mode, which comprises a shaft, the chamber mounted on the shaft, defined by a wall at least part of which is expandable, the chamber being associated with an inflation/deflation lumen for flow of the conductive fluid into the chamber after the catheter has been placed and for emptying the chamber after the heating has been accomplished.

Preferred embodiments have the following additional features. The device is sized for insertion into blood vessels or is sized to apply heat to the prostate. The chamber is a balloon. The electrical contacts are mounted directly upon the catheter shaft within the balloon. The electrical contacts comprise radiopaque markers. The conductors that apply potential to the contacts are enclosed within the shaft along its length, and exit the shaft through a lumen in the shaft inside of the balloon. The device includes a temperature sensor, and a temperature control circuit for controlling the output of the power supply in response to information received from the temperature sensor. The temperature sensor is located within the chamber, or outside the chamber in contact with tissue surrounding the chamber. The sensor and the rf power supply are operated alternately. The sensor may be a thermistor connected to one of the electrical contacts. The fluid is a saline solution, a conductive radiopaque fluid, or a mixture of such fluids.

In another aspect, the invention features a method of heating tissue, including the following steps: (1) inserting into a patient's body a deflated balloon catheter having a shaft, two or more electrical contacts enclosed within the balloon, and two or more conductors for connecting each of the electrical contacts to an r.f. power supply; (2) filling the chamber with an electrically conductive fluid preselected to produce resistive heating, and (3) applying an electrical potential at radio-frequency to the electrodes. The fluid is heated by radio frequency electric current flowing through it between the electrical contacts. The fluid in turn heats the surrounding tissue by heat transfer through the wall of the chamber.

In another aspect, the invention features an apparatus for heating tissue, having a shaft for insertion into a patient's body, a chamber mounted on the shaft and filled with a fluid, and a device for inducing localized boiling in the fluid. The boiling aids in convection of heat from the fluid to the surrounding tissue. In preferred embodiments, the device for inducing boiling in the fluid includes two electrical contacts enclosed within the balloon, a power supply for applying an electrical potential to the contacts, and a pair of conductors for connecting each of the contacts to the power supply. The fluid is electrically conductive and the fluid is heated by a radio frequency electric current flowing between the contacts, the fluid in turn heating surrounding tissue by heat transfer through the wall of the chamber. The apparatus further includes a temperature sensor, and a temperature control circuit for controlling the output of the power supply in response to information received from the temperature sensor. The temperature sensor may be a pressure transducer for measuring the pressure of the fluid, as a means of indirectly measuring the amount of heating of the fluid on of the surrounding tissue.

The direct, bipolar heating of the fluid within the balloon according to the invention allows for precise control of the temperature to which the fluid is heated, or of the temperature of an adjacent body site, and control of the duration of such heating, as is described below. The electrical contacts provide a very low profile means of heating the fluid, so that the deflated balloon can be easily inserted into or removed from very narrow passages within the patient's body.

DESCRIPTION OF THE PREFERRED EMBODIMENTS

We first briefly describe the drawings.

DRAWINGS

STRUCTURE

Figure 1:
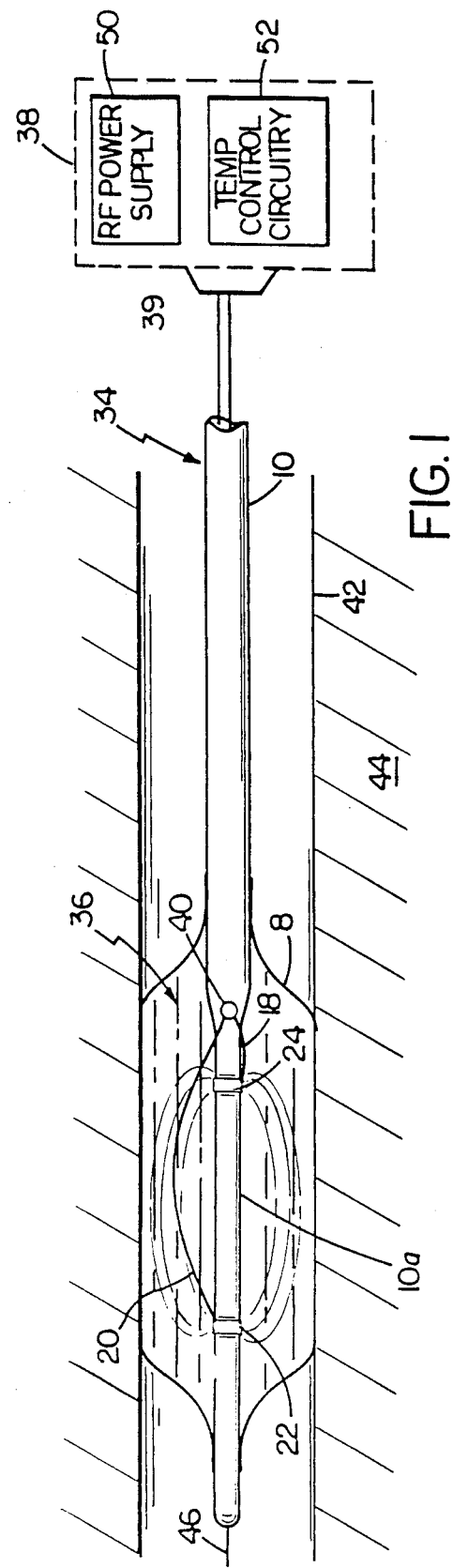
FIG. 1 shows a balloon catheter according to the invention.

In the embodiment of FIG. 1, balloon catheter 34 comprises a polyethylene teraphthalate (PET) balloon 8 mounted on nylon catheter shaft 10. The fully extended diameter of balloon 8, when inflated, ranges from 2 millimeters for coronary vascular procedures, to 20 or 35 millimeters for hyperthermia treatment of the prostate, esophagus or colon. The volume of the balloon ranges from ⅛ cc for the smallest balloon to 100 cc for the largest balloon. The wall thickness of balloon 8 is about 0.001 inch. Guidewire 46, which can extend past the distal end of the catheter, may be used to guide the catheter through the vascular system or luminal structure. Balloon 8 is fillable with an electrically conductive fluid 36 such as normal saline (0.9 percent NaCl in water), a conductive radiopaque fluid, or a mixture of saline solution and a radiopaque fluid. The exterior of the balloon is coated with a non-stick coating having a low coefficient of friction, such as silicone or polysiloxane.

Annular electrical contacts 22 and 24 inside of balloon 8 have internal diameters matching the portion 10a of the catheter shaft 10 which they surround and are bonded directly to the catheter shaft. The spacing between the contacts is approximately half the length of the balloon, and the spacing from the respective end of the balloon is approximately one fourth the length of the balloon, so that the balloon will heat evenly. While the dimensions of the contacts vary according to the nature of the medical procedure to be performed, in this embodiment it is preferable that the contacts be in the form of annular thin-wall bands having their axial length and diameter about equal. For the range of uses contemplated for this embodiment, the inner diameter of the smallest contact is about 0.050 inch, and the inner diameter of the largest contact is about 0.120 inch. The contacts present a low profile, having a radial thickness of approximately 0.002 inch. The contacts can be made of any conductive material that is compatible with the conductive solution and the conditions of use, but are preferably of a radiopaque metal such as platinum or tantalum, so that they may serve as radiopaque markers during placement of the catheter. Contacts 22 and 24 are preferably coated with tin, so that they may be soldered by means of tin solder to 34 gauge, multi-filament, copper wires 20 and 18, respectively. These wires, which are TEFLON-insulated, and have outer diameters of 0.012 inch, connect contacts 22 and 24, respectively, to opposite poles of current-controlled (constant current) radio-frequency power supply 50. Wires 20 and 18 are enclosed within catheter shaft 10 along its length, and exit catheter shaft 10 through lumen 40, which is located inside of balloon 8.

RF power supply 50 preferably operates at 650 kilohertz, but can be at any frequency within the range of about 100 kilohertz to 1 megahertz. Radio frequency power is important to use rather than direct or low frequency current, or microwave power, because the risk of a physiological response or electrocution response is reduced at RF frequencies above 100 kHz as compared with d.c. or low frequencies, and because microwave power would lead to radiative losses in wires 18 and 20, that can result, e.g. in unwanted heating of catheter shaft 10. The fluid 36, while selected to have resistive losses, has an electrical impedance low enough that it will conduct the current supplied by RF power supply 50 at voltages of about 100 volts or lower, so that there will be no arcing across insulated wires 18 and 20. For example, if the current I is set at 1 amp, and the impedance R between the electrodes, through the fluid is 100 ohms, the voltage V will be 100 volts according to $V=IR$, and the power P dissipated into the fluid will be 100 watts, according to $P=I^2R$. In general, where two electrodes are employed, the impedance between the electrodes will be less than 1000 ohms, preferably in the range of 50 to 500 ohms, and in the present embodiment most preferably at about 100 ohms.

In all events the shape of the balloon and the construction and spacing of the electrical contacts are preselected so that the electrical current is substantially confined to the interior of the balloon.

Catheter 34 plugs into RF power supply and temperature control circuitry 38 by means of a plug 39, that is keyed with respect to the particular size of balloon catheter it is associated with, to cause the power supply to operate at a maximum current of 1/10, ¼, ½ or 1 amp. Plug 39 has seven pins, three of which are needed to operate the catheter. During manufacture, a jumper connection is made within plug 39 between a selected two of the remaining four pins. The jumper connection indicates how much current, at maximum, the RF power supply 50 should produce, depending upon which pins the jumper connection connects. Thus, the user need only select the appropriate catheter 34, and need not be concerned about selecting the appropriate maximum current.

Figure 2:
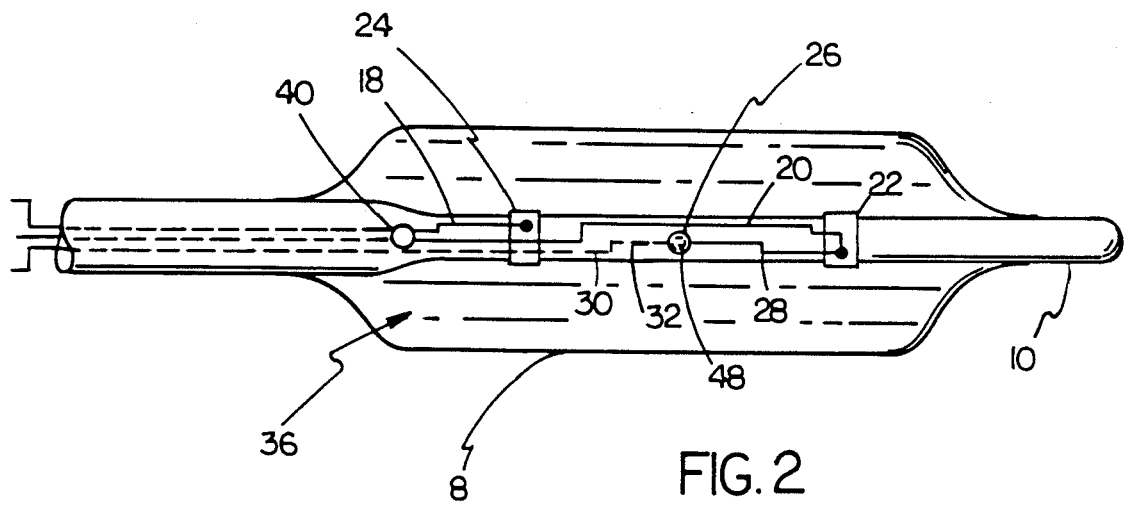
FIG. 2 is a detailed drawing of the balloon portion of the balloon catheter shown in FIG. 1, according to an embodiment of the invention in which a temperature sensing device is mounted inside the balloon.

Referring to FIG. 2, in one embodiment of the invention, a bead thermistor 26, 0.014 inch in diameter and 0.020 inch long, is mounted directly upon catheter shaft 10 between electrodes 22 and 24. Stainless steel thermistor lead 28 connects thermistor 26 with electrode 22. A 34 gauge, multi-filament, TEFLON coated, copper wire 30, outer diameter 0.012 inch, which is soldered to the other stainless steel thermistor lead 32, connects thermistor lead 32 with RF power supply and temperature control circuitry 38 via one of the pins of the plug. Thermistor 26 fits snugly on top of an opening 48 in the wall of catheter shaft 10 midway between electrodes 22 and 24. Wire 30 and thermistor lead 32 are enclosed within catheter shaft 10, and thermistor lead 32 connects with thermistor 26 through opening 48. An insulating coating of epoxy or urethane seals thermistor 26 on top of opening 48, and secures thermistor lead 28 to catheter shaft 10. Alternatively, thermistor lead 28 may be electrically connected to RF power supply and temperature control circuitry 28 in the same manner as thermistor lead 32, rather than being connected to electrode 22.

Figure 3:
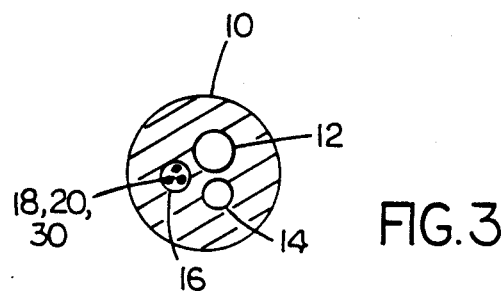
FIG. 3 is a transverse cross-section of the catheter shaft of the balloon catheter shown in FIG. 2.

Referring to FIG. 3, catheter shaft 10 has three lumens 12, 14, and 16. Lumen 12 extends from the proximal end of catheter shaft 10 to the distal end, and provides a conduit for guidewire 46. Lumen 14 extends from the proximal end of catheter shaft 10 to an outlet in the inside of balloon 8, and provides a conduit for fluid 36 as balloon 8 is inflated and deflated. Lumen 16 extends from the proximal end of catheter shaft 10 to the inside of balloon 8, and provides a conduit for wires 18 and 20, which exit lumen 16 through opening 40 in the wall of catheter shaft 10, and also provides a conduit for wire 30 and thermistor lead 32 through opening 48 in catheter shaft 10 that is located directly below thermistor 26, as mentioned above.

Figure 4:
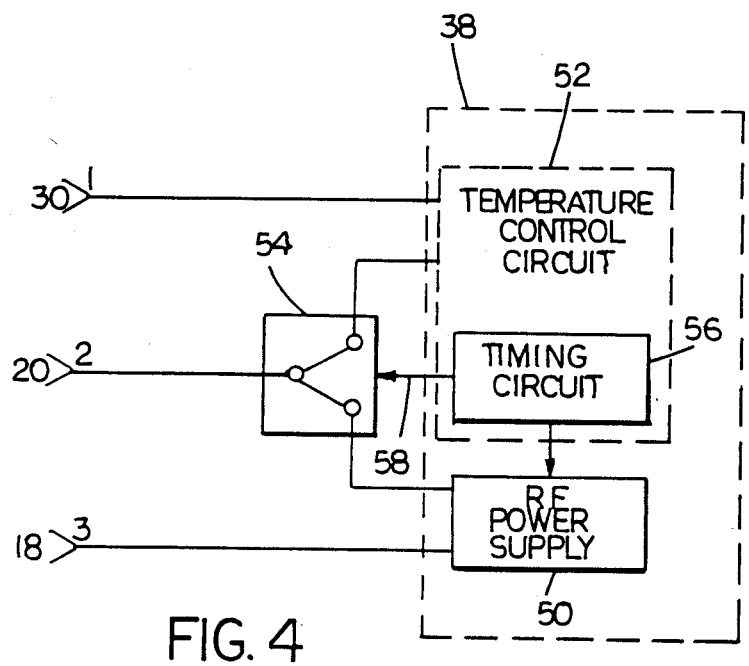
FIG. 4 is a block diagram of the RF power supply and temperature control circuitry according to the embodiment of the invention of FIG. 2.

Referring to FIG. 4, RF power supply and temperature control circuitry 38 consists of RF power supply 50, temperature control circuit 52, and solid state switch 54. Wire 18 connects electrode 24 with RF power supply 50, and wire 30 connects thermistor 26 with temperature control circuit 52. Timing circuit 56 of temperature control circuit 52 toggles hold/NOT sample line 58 so that solid state switch 54 toggles back and forth, whereby wire 20 functions alternately as a lead connecting RF power supply 50 with electrode 22 and as a lead connecting temperature control circuit 52 with thermistor 26. (Recall that electrode 22 and thermistor 26 are connected by wire 28.) The temperature sensing period is 1 percent of the 60 hertz cycle. When solid state switch 54 connects wire 20 with temperature control circuit 52, temperature control circuit 52 determines how much power, at maximum, RF power supply 50 should supply when solid state switch 54 next connects wire 20 with RF power supply 50. By thus multiplexing between temperature sensing and application of current to the electrodes, the temperature control circuitry eliminates the possibility that thermistor 26 will pick up RF noise from the electrodes 22 and 24.

Figure 5:
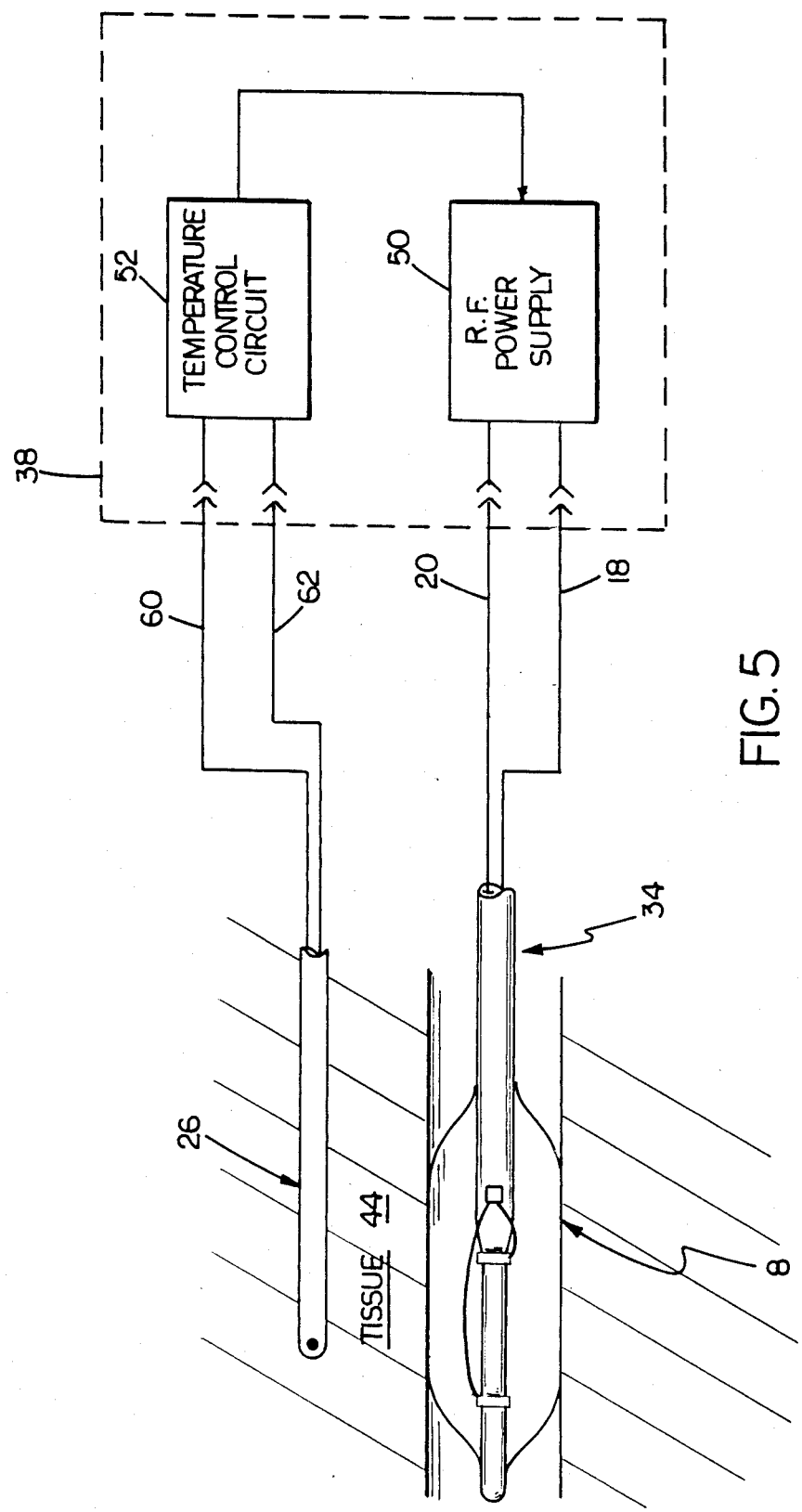
FIG. 5 is a block diagram of the RF power supply and temperature control circuitry according to an embodiment of the invention in which a temperature sensor is placed in direct contact with the tissue surrounding the balloon.

Referring to FIG. 5, another embodiment of the invention is shown in which temperature sensor 26 is placed in direct contact with tissue 44, outside of balloon catheter 34. Wires 60 and 62 connect temperature sensor 26 with temperature control circuit 52, and wires 20 and 18 connect electrodes 22 and 24 respectively with RF power supply 50. Temperature control circuit 52 regulates RF power supply 50 in response to the input from temperature sensor 26.

Figure 6:
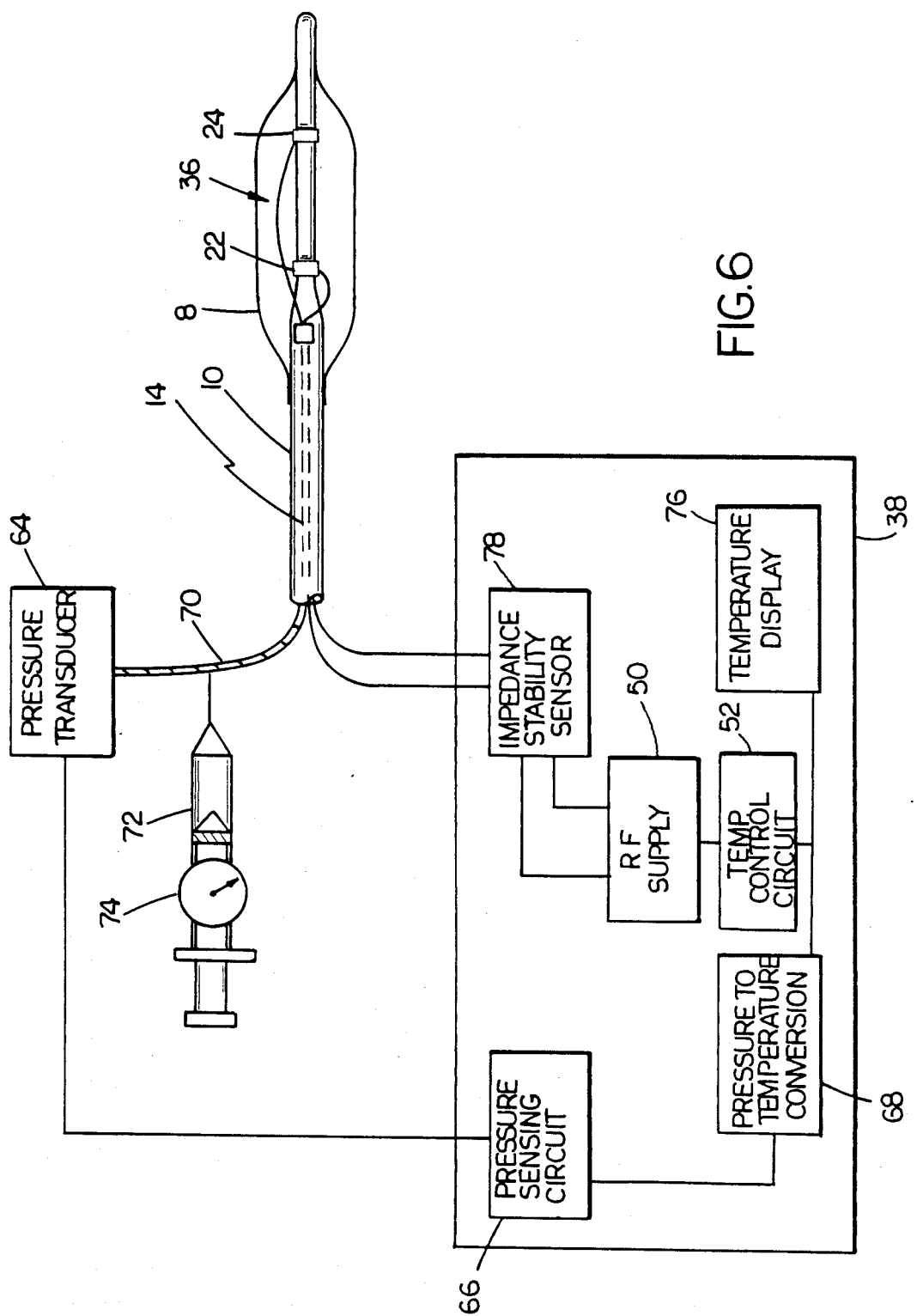
FIG. 6 is a block diagram of the RF power supply and temperature control circuitry according to an aspect of the invention in which a pressure transducer is used inside of the balloon as a means of indirectly measuring the amount of heating of surrounding tissue.

Referring to FIG. 6, another embodiment of the invention is shown in which the temperature sensor consists of a pressure transducer 64 in conjunction with pressure sensing circuit 66 and pressure-to-temperature conversion circuit 68. In this embodiment, the electrodes 22 and 24 are small enough that the electric current density in the immediate vicinity of the electrodes can induce localized boiling, which aids in the convection of heat from the electrodes to the surrounding tissue 44. The balloon material is heat-set at a temperature in excess of 100° Celsuis, so that the balloon material remains dimensionally stable when the fluid 36 within the balloon 8 boils at about 100° Celsius. A flexible tube 70 provides a conduit for fluid into lumen 14 of catheter shaft 10. Inflator 72 is used to inject fluid into flexible tube 70 until a desired pressure is obtained, as indicated by pressure gauge 74. When RF power supply 50 is activated, the high electric field density in the immediate vicinity of each of the electrodes 22, 24 can induce localized boiling of fluid 36. As the fluid 36 heats up, the boiling increases in intensity. The boiling causes the pressure inside balloon 8 to increase. The increase in pressure is measured by pressure transducer 64, as an indirect indication of the amount of heating of the fluid 36, according to phase change pressure/temperature relationships. Temperature control circuit 52 regulates RF power supply 50 in response to the input obtained from pressure-to-temperature conversion circuit 68. Temperature display circuit 76 displays the temperature obtained from pressure-to-temperature conversion circuit 68. Impedance stability sensor 78 detects the initiation of boiling by sensing the instability of catheter impedance due to the formation of vapor at the surfaces of electrodes 22 and 24.

Figure 7:
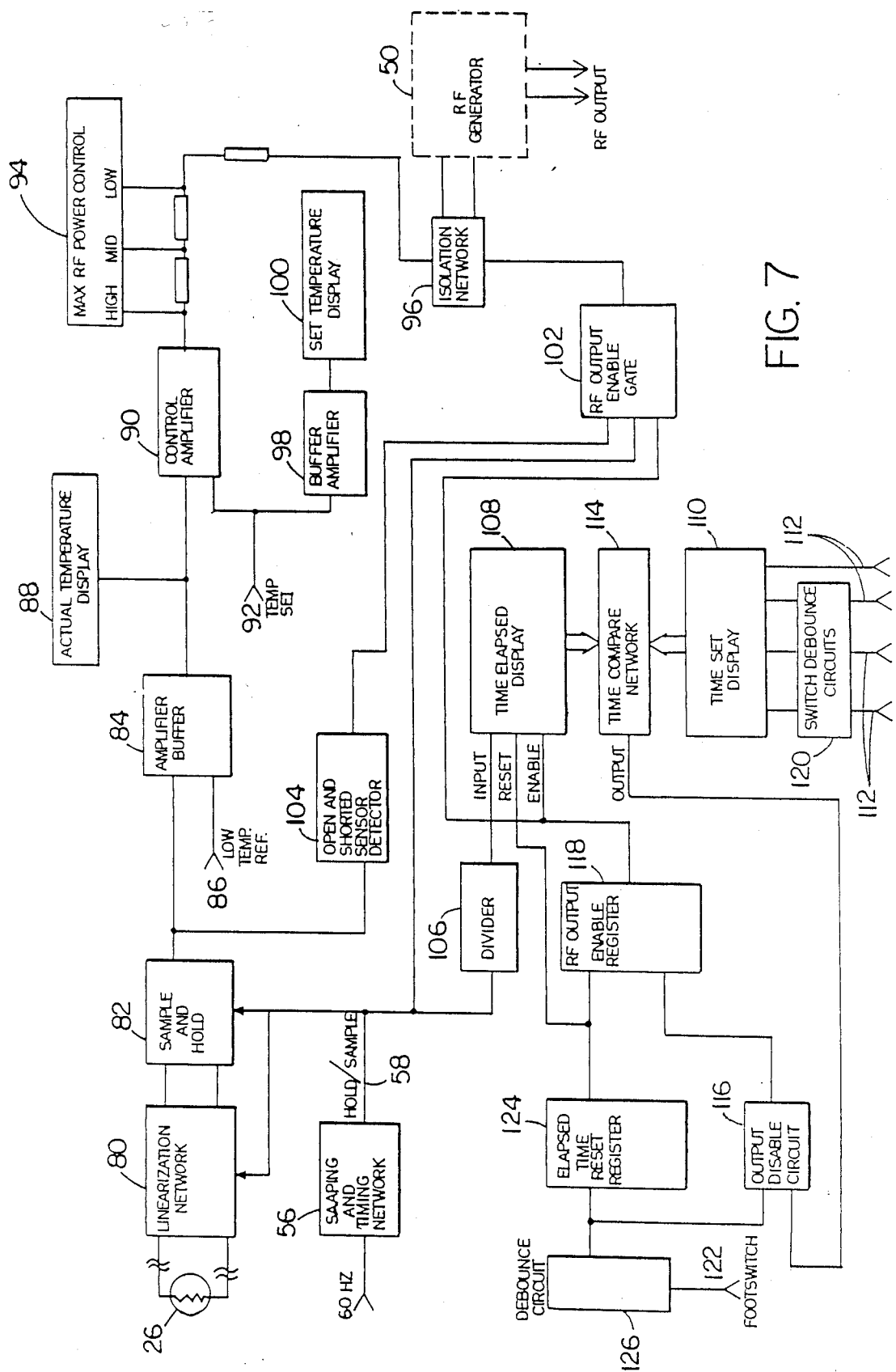
FIG. 7 is a detailed block diagram of the temperature control circuit shown in FIGS. 4, 5 and 6.

Referring to FIG. 7, in temperature control circuit 52, linearization network 80 linearizes the input signal from temperature sensor 26 and delivers the linearized signal to sample and hold register 82. The signal is deliver to amplifier buffer 84 having low-temperature reference 86. Actual temperature display circuit 88 displays the output of amplifier buffer 84. Control amplifier 90 compares the output of amplifier buffer 84 with a temperature set voltage 92 that is set by the user. The maximum RF power contol circuit 94 receives the output of control amplifier 90 and determines the level of RF power, at maximum, that the RF power supply 50 should produce. The signal from the maximum RF power control circuit 94 is received by isolation network 96, which interfaces with RF power supply 50. The temperature set voltage 92 is received by buffer amplifier 98 and displayed by set temperature display 100.

Timing circuit 56 toggles hold/NOT sample line 58 at 60 hertz, so that hold/NOT sample line 58 is low during 1 percent of the cycle and high during the other 99 percent of the cycle. Hold/NOT sample line 58 is low when signals from temperature sensor 26 are being sampled and high when signals from temperature sensor 26 are not being sampled. Hold/NOT sample line 58 is received by RF output enable gate 102. The output of sample and hold register 82 is processed by open and short sensor detector 104 to determine whether a sensor malfunction, such as a shorted or open sensor, has occurred. The output of open and shorted sensor detector 104 is received by RF output enable gate 102. RF output enable gate 102 delivers a signal to isolation network 96, which turns off RF power supply 50 when there has been a sensor malfunction or when signals from temperature sensor 26 are being sampled.

Divider 106 receives hold/NOT sample line 58 and delivers its output to time elapsed display 108. Time set display 110 displays the time indicated by time set switches 112, which are set by the user. Time compare network 114 compares the elapsed time with the time set by the user, and delivers an output signal to output disable circuit 116. The output of output disable circuit 116, which is active only when the elapsed time is less than the time set by the user, is delivered to RF output enable register 118. RF output enable register 118 in turn delivers the signal to the enable input to time elapsed display 108, and also to RF output enable gate 102, so that RF power supply 50 may be turned off when the time set by the user has elapsed. Switch debounce circuits 120 are provided for time set switches 112.

The user must depress footswitch 122 in order for RF power supply 50 to operate. While footswitch 122 is activated, and while the elapsed time is less than the time set by the user, output disable circuit 116 delivers a signal to RF output enable register 118, which in turn delivers the signal to the enable input of time elapsed display 108, and also to RF output enable gate 102 so that rf power supply 50 may be turned on. Deactivation of footswitch 122 causes a signal to pass through elapsed time reset register 124, in order to reset time elapsed display 108 and in order to reset RF output enable register 118. The resetting of RF output enable register 118 causes RF output enable gate 102 to turn off RF power suppy 50. Debounce circuit 126 is provided for footswitch 122.

Operation

Referring to FIG. 1, balloon catheter 34 may be used as a heat source during or after angioplasty to seal the splitting of the intimal layers of the wall of blood vessel 42 that occurs during angioplasty, and to mold the vessel wall. The blood vessel may be a coronary artery, or a peripheral artery such as an iliac, femoral, renal, carotid, or popliteal artery. The user first preselects the desired therapeutic temperature (temperature set voltage 92, FIG. 7), and sets the length of time for which balloon 8 is to be heated (time set switches 112, FIG. 6). A percutaneous insertion is made with a needle, and guide wire 46 is introduced into the blood vessel 42. Balloon catheter 34 follows the wire. If balloon 8 contains conductive radiopaque fluid, the location of balloon 8 can be monitored by means of fluoroscopy. Balloon 8 is inflated through lumen 14 with either saline, a conductive radiopaque fluid, or a mixture of saline and a radiopaque fluid, to a pressure of 4 to 17 atmospheres, in order to expand the wall of blood vessel 42. The balloon remains inflated for about 20 seconds or longer, depending on the particular blood vessel upon which the angioplasty is being performed. Either during or after the plastic deformation of the vessel wall, with balloon 8 inflated to at least a low level of pressure, the user depresses footswitch 122 (FIG. 7) to initiate the bi-polar heating between the electrodes 36. Heat is dissipated into the fluid according to the formula $P=I^2R$ where P is the power that is dissipated into the fluid, I is the current that is passed through the electrodes, and R is the resistance of the fluid. The heat from the fluid is conducted across the balloon wall into the surrounding tissue 44. For angioplasty procedures, RF power supply 50 supplies a maximum current of ¼ amp, and the power dissipated into fluid 36 is about 10 to 25 watts. The fluid will heat to the temperature set by the user, which may be in the range of 45° Celsius to 80° Celsius. Heating will continue until the time set by the user has elapsed, or until the user deactivates footswitch 122.

The balloon catheter may also be used to perform glazing or smoothing of the vessel wall, whereby the baloon 8 is inflated to make light contact with the wall of blood vessel 42, footswitch 122 is activated by the user to initiate heating of the balloon, and the catheter 34 is guided through blood vessel 42 to glaze or smooth the plaque on the vessel wall. The balloon catheter may also be used to dehydrate, compress, and mold plaque to improve patency.

Catheters according to the invention can be used in nonvascular applications such as hyperthermia treatment of benign or malignant tumors, or enlargement of the prostate gland. Hyperthermic effects begin at about 44° Celsius. Heat from balloon 8 destroys the undesired cells, which are eventually absorbed into the patient's body. When a catheter according to the invention is used in such nonvascular applications, the balloon 8 may be large enough that no temperature sensing device is needed, and the fluid 36 can be left to boil of the electrodes without the buildup of excessive pressure within the balloon. The fluid will begin to boil locally in about 5 seconds if the balloon has a diameter of 4 millimeters.

Other embodiments are within the following claims.

We claim:

1. Device for heating tissue, comprising
   a chamber constructed for insertion into a patient's body,
   an electrically conductive fluid preselected for resistive heating for filling the chamber,
   a plurality of spaced electrical contacts enclosed within the chamber and a corresponding plurality of conductors for connecting the electrical contacts to a power supply for applying a radio frequency electrical potential between the contacts, said contacts being exposed to the fluid-containing space of said chamber so that said radio frequency electrical potential can cause current to flow through fluid between the contacts, said chamber and said contacts being cooperatively constructed and arranged to cause said current to be confined to said fluid within the chamber,
   whereby on the basis of $I^2R$ losses of said radio frequency electric current flowing between the electrical contacts, the fluid can be heated and the fluid in turn can heat the surrounding tissue by thermal conduction through a wall of the chamber.

2. The device of claim 1 wherein said chamber is defined by an expandable wall, the chamber adapted to be empty and the expandable wall collapsed at the time of introduction into the patient and wherein a conduit is adapted to fill the chamber with said fluid after introduction of the chamber into the patient's body.

3. The device of claim 1 or 2 wherein the chamber is defined by an inflatable balloon.

4. The device of claim 1 wherein said electrical contacts are radiopaque and serve as radiopaque markers.

5. The device of any of the claims 1 wherein the impedance between a pair of said electrodes, when said chamber is filled with said preselected fluid, is less than 1000 ohms.

6. The device of claim 5 wherein said impedance is in the range of 50 to 500 ohms.

7. The device of any of the claim 1 including a power supply constructed to operate at a frequency between 100 khz and 1 Mhz.

8. The device of claim 7 wherein the electrical potential applied across the contacts by the power source is about 100 volts or less.

9. The device of claim 7 further comprising
   a temperature sensor, and
   a temperature control circuit for controlling the output of the power supply in response to information received from the temperature sensor.

10. The device of any of the claim 1 wherein a temperature sensor constructed to sense the temperature of said fluid for controllinq the application of said electrical potential to said contacts is located within the chamber.

11. The device of any of the claim 1 associated with an temperature sensor located outside the chamber in contact with tissue surrounding the chamber for controlling the application of said electrical potential to said contacts is located within the chamber.

12. The device of any of the claims 1 wherein said chamber is filled with a saline solution.

13. The device of any of the claims 1 wherein said chamber is filled with a fluid that is radiopaque.

14. The device of any of the claims 1 sized and constructed for insertion into a blood vessel.

15. The device of any of the claim 1 sized and constructed for insertion into the body to apply heat to the prostate gland.

16. The device of any of the claim 1 wherein said chamber is coated with a coating that prevents said chamber from sticking to said tissue.

17. The device of any of the claim 1 including a power supply adapted to apply said current at a level sufficient to cause localized boiling of said fluid at said electrical contacts, to cause mixing of the fluid in said chamber and produce uniform heating of the chamber wall.

18. The device of claim 17 including a pressure transducer exposed to sense fluid pressure in said chamber and means constructed and arranged to control the energy applied to said electrical contacts in response to information received from the pressure transducer.

19. The device of any of the claim 1 associated with a power supply controlled by a thermister sensor, and a control constructed and arranged to operate alternately in a power application mode in which rf potential is applied to said contacts and a sensing mode during which application of rf potential to said contacts is disrupted 20. The device of any of the claim 1 including a thermister exposed to fluid in said chamber, said thermister connected to one of said electrical contacts, said device adapted to be used with a power supply controlled to alternately apply potential to said electrical contacts and to sense the temperature of the fluid in the absence of rf potential on the contacts.

21. A method for heating tissue, comprising inserting into a patient's body a chamber containing electrically conductive fluid preselected for resistive heating, there being a plurality of spaced electrical contacts encodes within the chamber and a corresponding plurality of conductors for connecting the electrical contacts to a power supply for applying a radio frequency electrical potential to the contacts, said contacts being exposed to the fluid-containing space of said chamber so that said radio frequency electrical potential can cause current to flow through fluid between the contacts, said chamber and said contacts being cooperatively constructed and arranged to cause said current to be confined to said fluid within the chamber, and applying radio frequency potential between said electrical contacts, whereby on the basis of $I^2R$ losses of said radio frequency electric current flowing between the electrical contacts, the fluid is heated and the fluid in turn heats the surrounding tissue by thermal conduction through a wall of the chamber.

22. The method of claim 21, wherein said radio frequency potential applied across said contacts is at frequency in the range between about 100 khz and 1 Mhz.

23. The method of claim 21, including controlling the electrical current between the electrical contacts to induce localized boiling at the contacts.

24. A method of constant temperate heating, comprising inserting into a patient's body a chamber containing electrically conductive fluid preselected for resistive heating, there being a plurality of electrical contacts enclosed within the chamber and a corresponding plurality of conductors for connecting the electrical contacts to a power supply for applying a radio frequency electrical potential to the contacts, said contacts being exposed to the fluid-containing space of said chamber so that said radio frequency electrical potential can cause current to flow through fluid between the contacts, said chamber and said contacts being cooperatively constructed and arranged to cause said current to be confined to said fluid within the chamber, applying radio frequency potential, between said electrical contacts, monitoring temperature at a point influenced by the temperature of said liquid and in response thereto controlling the radio frequency energy applied to said electrical contacts to maintain said temperature constant, whereby on the basis of $I^2R$ losses of said controlled radio frequency electric current flowing between the electrical contacts, the fluid is heated and the fluid in turn heats the surrounding tissue by thermal conduction through a wall of the chamber.

25. The method of claim 24 wherein said chamber comprises a balloon on a catheter introduced into a lumen or cavity of the body.

26. The method of claim 24 or 25 wherein temperature at a point in the body adjacent said chamber is monitored and used to control the application of energy to said electrodes to maintain temperature at said point constant for a selected duration, on the basis of thermal transfer from liquid heated in said balloon to said point.

27. The method of claim 24 or 25 wherein temperature of the liquid in said chamber is monitored and used to control the application of energy to said electrodes to maintain temperature of said fluid constant at a set point whereby it is assured that tissue in the vicinity of said chamber is not heated above said set point.

* * * * *

UNITED STATES PATENT AND TRADEMARK OFFICE
CERTIFICATE OF CORRECTION

PATENT NO. : 4,955,377
DATED : September 11, 1990
INVENTOR(S) : Charles D. Lennox, et al It is certified that error appears in the above-identified patent and that said Letters Patent is hereby corrected as shown below:

Column 3, line 12, "!.0." should be --10--.

Coluln 8, line 52, "controllinq" should be --controlling--.

Signed and Sealed this

Twentieth Day of October, 1992

Attest:

DOUGLAS B. COMER

Attesting Officer     Acting Commissioner of Patents and Trademarks

UNITED STATES PATENT AND TRADEMARK OFFICE
CERTIFICATE OF CORRECTION

PATENT NO. : 4,955,377
DATED : September 11, 1990
INVENTOR(S) : Charles D. Lennox, et al Page 1 of 3

It is certified that error appears in the above-indentified patent and that said Letters Patent is hereby corrected as shown below:

Column 3, line 12, "!.0." should be --10--.

Column 8, line 52, "controllinq" should be --controlling--.
On the title page: Item [56]
Under "References Cited" insert:

U.S. Patent Document Numbers:

```
   612,724,  10/18/98, Hamilton
 2,032,859,  3/03/36,  Wappler
 2,043,083,  6/02/36,  Wappler
 2,078,686,  7/29/35,  Rowe
 2,126,070,  8/09/38,  Wappler
 4,197,860,  4/15/80,  Sterzer
 4,204,549,  5/27/80,  Paglione
 4,311,154,  1/19/82,  Sterzer et al.
 4,522,194,  6/11/85,  Normann
 4,528,991,  7/16/85,  Dittmar et al.
 4,612,940,  9/23/86,  Kasevich et al.
 4,641,649,  2/10/87,  Walinsky et al.
 4,643,186,  2/17/87,  Rosen et al.
```

UNITED STATES PATENT AND TRADEMARK OFFICE
CERTIFICATE OF CORRECTION

PATENT NO. : 4,955,377

DATED : September 11, 1990

INVENTOR(S) : Charles D. Lennox, et al

It is certified that error appears in the above-indentified patent and that said Letters Patent is hereby corrected as shown below:

U.S. Patent Document Numbers 4,662,383, 5/05/87, Sogawa et al.
   4,709,698, 12/01/87, Johnston et al.
   4,754,752, 7/05/88, Ginsburg et al.

Foreign Patent Document Numbers:

342,419, 2/05/31, Great Britain
   0,182,689, 5/28/86, EPA (European)

Other Documents:

Zeiher, "A Prototype RF-Heated 'Hot Balloon' PTCA – Cather: Design Param and In Vitro Tissue Studies, <u>Cir. Supp. Abstracts from 61st Scientific Sessions</u>, Vol. 78, No. 14, October, 1988.

Brezovich et al., "A Practical System For Clinical Radiofrequency Hypothermia," <u>Int. Journ. of Radiation Oncology</u>, Vol. 2, No. 3, March.

UNITED STATES PATENT AND TRADEMARK OFFICE
CERTIFICATE OF CORRECTION

PATENT NO. : 4,955,377
DATED : September 11, 1990
INVENTOR(S) : Charles D. Lennox, et al It is certified that error appears in the above-indentified patent and that said Letters Patent is hereby corrected as shown below:

Other Documents

Astrahan et al., "Temperature Measurement For MW Antenna," Temp. Meas.

Trembly et al., "Practical Embedded Insulated Antenna for Hypothermia", IEEE Cat. No. 82CH1747-5, July 1982, pp. 105-108.

Szwarnowski, "A Thermometer for Measuring Temperatures in the Presence of Electromagnetic Fields," Clin. Phys. Physiol. Meas., 1983 Vol. 4, No. 1, pp. 79-84, Great Britain.

Samaras et al., "Correction of Microwave-Induced Thermistor Sensor Errors," Med. Phys., 10(3) May/June 1983, Am. Assoc. Phys. Med.

Luxtron Corp., "Small Business Innovation Research Program", 1984, pages 1-4.

Signed and Sealed this

Fourteenth Day of September, 1993

Attest:

BRUCE LEHMAN

Attesting Officer    Commissioner of Patents and Trademarks